(12) United States Patent  
Byrd

(10) Patent No.: US 6,612,307 B2
(45) Date of Patent: Sep. 2, 2003

(54) OXYGEN CONSERVER

(75) Inventor: Douglas S. Byrd, Copley, OH (US)

(73) Assignee: Western/Scott Fetzer Company, Westlake, OH (US)

( * ) Notice: Subject to any disclaimer, the term of this patent is extended or adjusted under 35 U.S.C. 154(b) by 0 days.

(21) Appl. No.: 09/932,853

(22) Filed: Aug. 17, 2001

(65) Prior Publication Data

US 2002/0073998 A1 Jun. 20, 2002

Related U.S. Application Data

(60) Provisional application No. 60/231,604, filed on Sep. 11, 2000.

(51) Int. Cl.$^7$ .......................... A61M 16/00; A62B 7/04; F16K 31/26
(52) U.S. Cl. .......................... 128/204.26; 128/204.22; 128/204.23; 128/204.29; 128/205.24
(58) Field of Search .................. 128/204.23, 203.14, 128/204.22, 204.26, 204.29, 205.24

(56) References Cited

U.S. PATENT DOCUMENTS

| | | | | | |
|---|---|---|---|---|---|
| 4,006,742 A | * | 2/1977 | Flynn | ..................... | 128/205.24 |
| 4,054,133 A | * | 10/1977 | Myers | ..................... | 128/204.26 |
| 4,127,129 A | * | 11/1978 | Cramer | ..................... | 128/204.28 |
| 4,686,974 A | * | 8/1987 | Sato et al. | ..................... | 128/204.23 |
| 5,137,017 A | * | 8/1992 | Salter | ..................... | 128/204.18 |
| 5,230,330 A | * | 7/1993 | Price | ..................... | 128/203.11 |
| 5,307,795 A | * | 5/1994 | Whitwam et al. | ..................... | 128/204.23 |
| 5,360,000 A | * | 11/1994 | Carter | ..................... | 128/204.26 |
| 5,398,714 A | * | 3/1995 | Price | ..................... | 137/102 |
| 5,666,945 A | * | 9/1997 | Davenport | ..................... | 128/200.14 |
| 5,881,725 A | * | 3/1999 | Hoffman et al. | ..................... | 128/204.26 |
| 6,116,242 A | * | 9/2000 | Frye et al. | ..................... | 128/205.24 |
| 6,318,366 B1 | * | 11/2001 | Davenport | ..................... | 128/204.18 |
| 6,325,062 B1 | * | 12/2001 | Sosiak | ..................... | 128/200.23 |
| 6,378,520 B1 | * | 4/2002 | Davenport | ..................... | 128/204.18 |
| 6,412,483 B1 | * | 7/2002 | Jones et al. | ..................... | 128/205.11 |
| 6,425,396 B1 | * | 7/2002 | Adriance et al. | ..................... | 128/204.26 |

FOREIGN PATENT DOCUMENTS

| | | |
|---|---|---|
| WO | WO 87/02590 | 5/1987 |
| WO | WO 97/11734 | 4/1997 |
| WO | WO 01/41857 | 6/2001 |

* cited by examiner

*Primary Examiner*—Weilun Lo
*Assistant Examiner*—Michael Mendoza
(74) *Attorney, Agent, or Firm*—Jones Day

(57) ABSTRACT

An oxygen conserver having sensing and delivery ports simultaneously connected with a patient by a dual cannula. Inhalation by a patient produces a partial vacuum to move a sensing diaphragm to a venting position and cause a delivery diaphragm to move to an open position for supplying oxygen to the patient through the delivery port. A manually operable control valve enables continuous oxygen flow through the delivery port independently of operation of the sensing diaphragm.

14 Claims, 5 Drawing Sheets

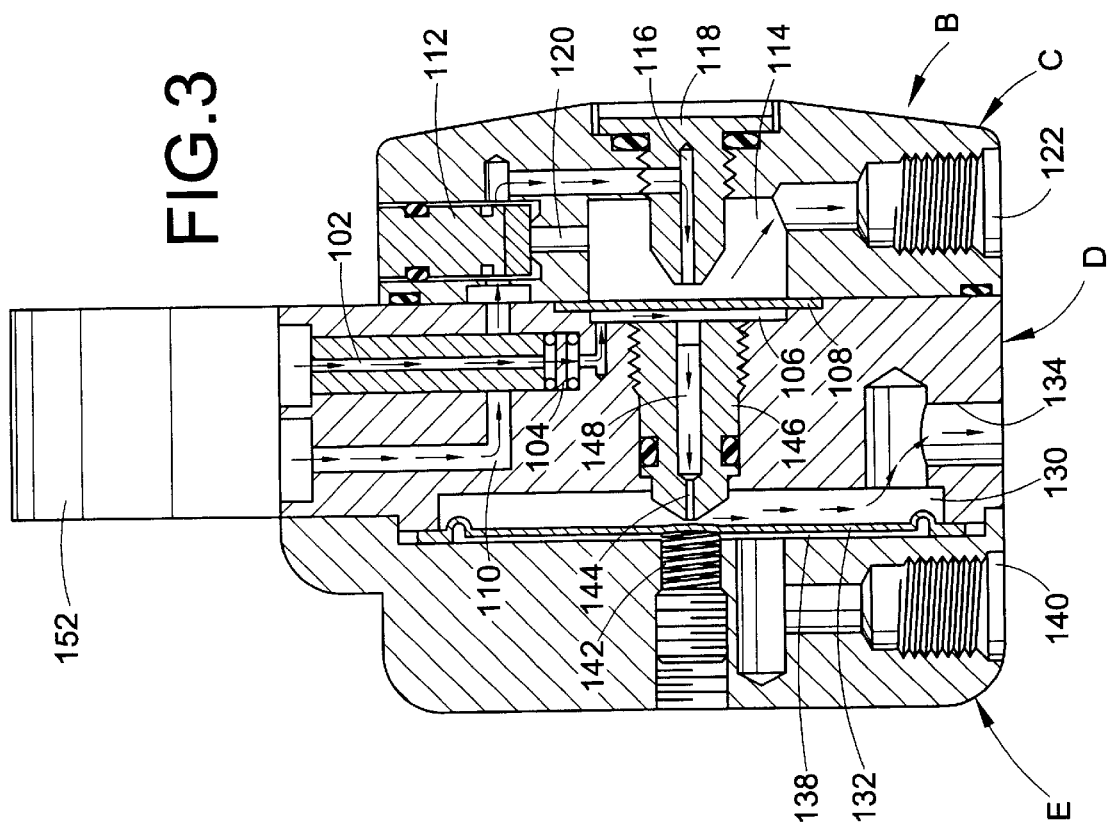
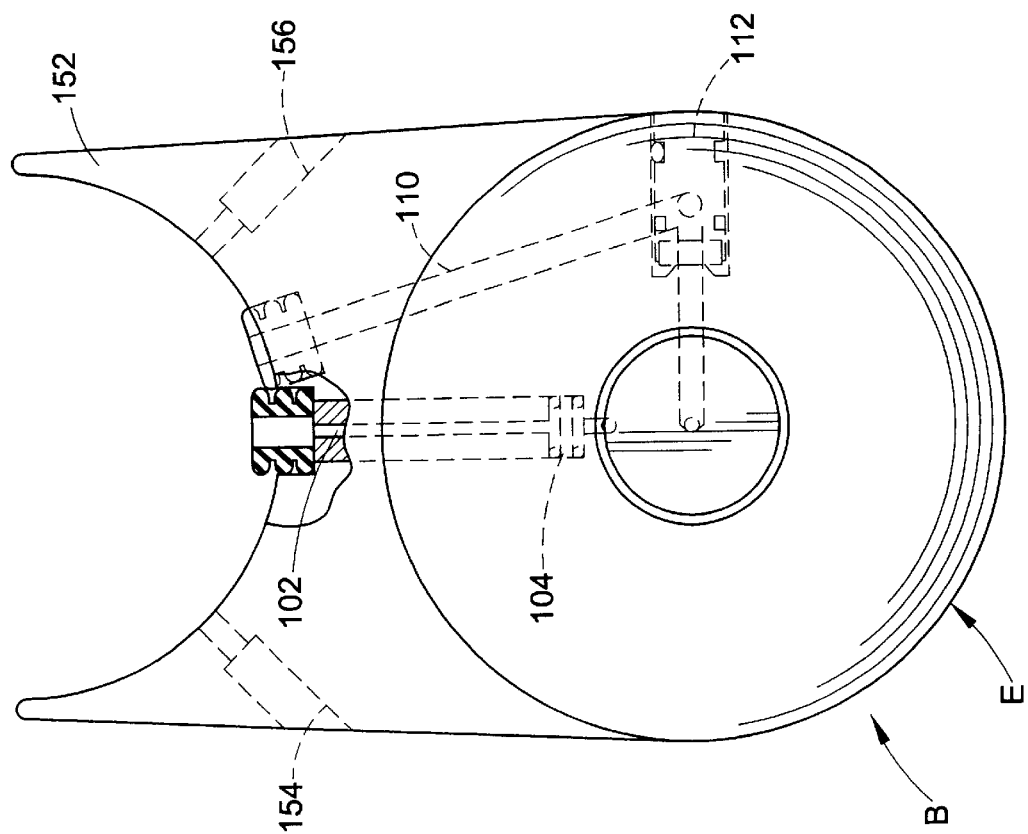

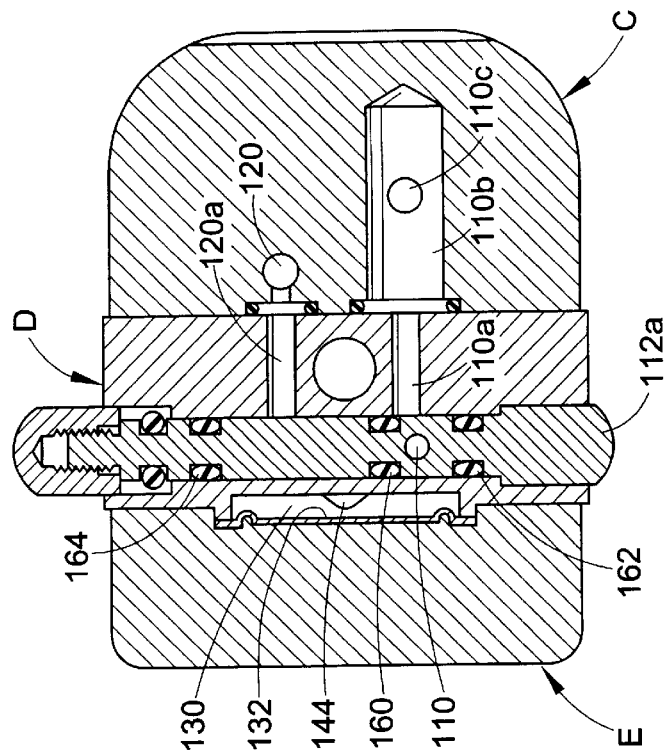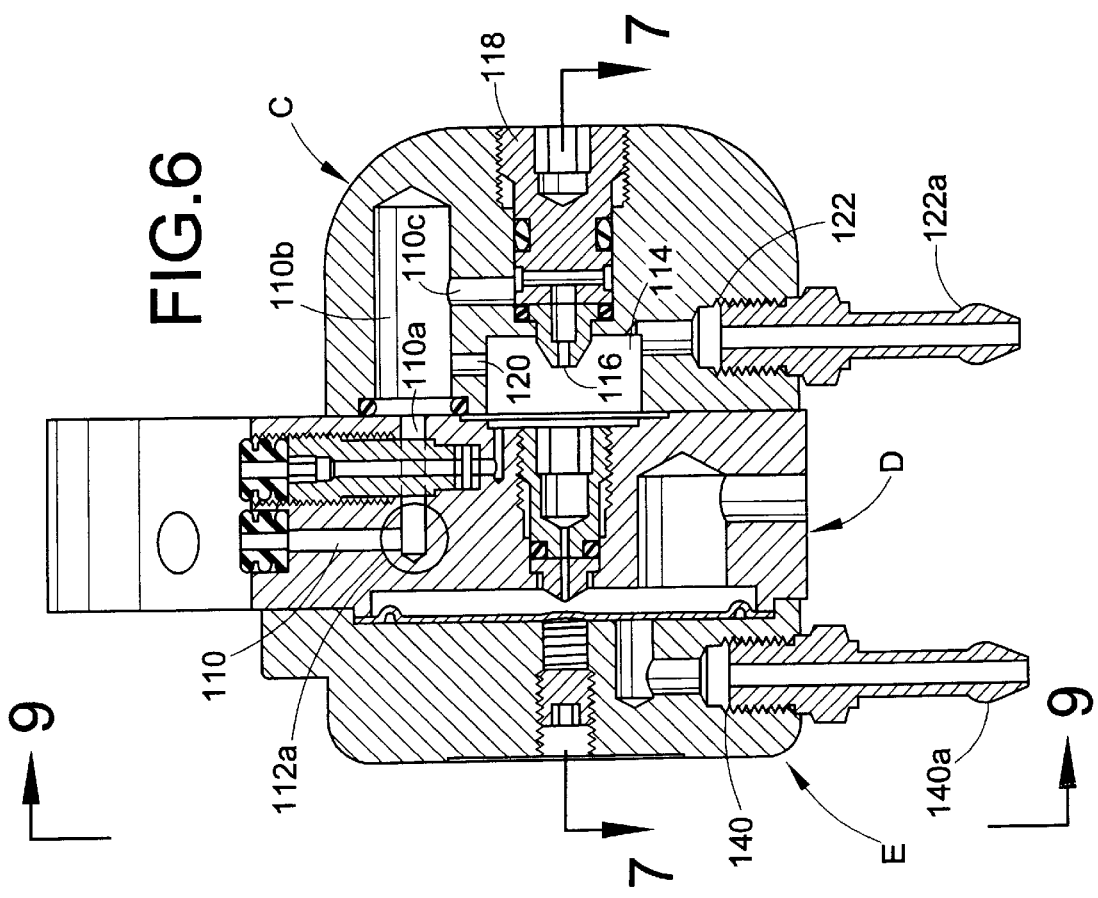

OXYGEN CONSERVER

RELATED APPLICATIONS

This application claims subject matter disclosed in U.S. provisional application Ser. No. 60/231,604 filed Sep. 11, 2000, the benefit of the filing date of which is hereby claimed.

BACKGROUND OF THE INVENTION

This application relates to the art of gas flow controls and, more particularly, to such controls that are capable of providing either a continuous or intermittent flow of gas. The invention is particularly applicable to oxygen conserving devices that are used to supply medicinal oxygen to a patient and will be described with specific reference thereto. However, it will be appreciated that the invention has broader aspects and that at least certain features thereof may be used for other purposes in other gas flow control devices.

Continuous supply of oxygen to a patient wastes oxygen. Therefore, demand valves have been developed to conserve oxygen by cutting off oxygen flow during a patient's exhalation cycles and starting oxygen flow during a patient's inhalation cycles. It would be desirable to have a simplified and sensitive oxygen conserving unit that is reliable and can be used with conventional pressure flow regulators without requiring extensive modifications.

SUMMARY OF THE INVENTION

An oxygen conserving device in accordance with the present application has a pair of ports that simultaneously are connected with a patient by a dual cannula. The tubes of the dual cannula may be side-by-side or coaxial. In a conserving mode, inhalation by the patient causes a diaphragm valve to open for delivering oxygen to the patient.

The oxygen conserving device is assembled from three sections including a delivery section, a central supply section and a sensing section. The three sections are suitably bolted or otherwise secured together.

The conserving device includes an oxygen delivery port and a sensing port for sensing inhalation by a patient.

The oxygen delivery port delivers oxygen from an oxygen delivery chamber that has an oxygen metering flow inlet. A delivery diaphragm opens and closes the oxygen metering flow inlet, and an oxygen supply pressure chamber is on the opposite side of the delivery diaphragm from the oxygen delivery chamber. Pressurization of the supply pressure chamber moves the delivery diaphragm to a position closing the oxygen metering flow inlet.

An atmospheric vent passage from the supply pressure chamber is normally closed by a sensing diaphragm. The sensing diaphragm responds to patient inhalation by opening the vent passage to vent the supply pressure chamber to atmosphere and cause the delivery diaphragm to open the oxygen metering flow inlet to the oxygen delivery chamber.

A manually operable control valve is selectively operable to provide continuous metering flow of oxygen to the oxygen delivery chamber through a continuous metering flow passage. The sensing and delivery diaphragms may continue to cycle with patient inhalation/exhalation but this does not affect the continuous metering flow when the control valve is in the continuous metering flow position.

An oxygen delivery device in accordance with the present application includes a delivery diaphragm and a sensing diaphragm. The periphery of the delivery diaphragm is sealed between the delivery and supply sections, and the sensing diaphragm is sealed between the supply and sensing sections.

An oxygen delivery chamber is provided in the delivery section on one side of the delivery diaphragm and a supply pressure chamber is provided in the supply section on the opposite side thereof. The oxygen delivery chamber has an oxygen metering flow inlet and an oxygen delivery outlet.

A sensing chamber having a sensing port is provided in the sensing section on one side of the sensing diaphragm, and an atmospheric chamber having an atmospheric vent port is provided in the supply section on the opposite side of the sensing diaphragm.

A vent passage connects the supply pressure chamber with the atmospheric chamber, and the sensing diaphragm normally is biased in a direction to close the vent passage. Pressure in the supply pressure chamber moves the delivery diaphragm to a position closing the oxygen metering flow passage to the oxygen delivery chamber.

The sensing diaphragm is movable to a position opening the vent passage in response to a partial vacuum in the sensing chamber produced by a patient's inhalation through a cannula connected to the sensing port so that the supply pressure chamber is vented to atmosphere through the vent passage. This causes movement of the delivery diaphragm to a position opening the oxygen metering flow inlet for supplying oxygen to the delivery chamber and through the oxygen delivery outlet to a patient.

It is a principal object of the present application to provide an oxygen conserving device having two ports that simultaneously are connected with a patient by a dual cannula.

It is another object of the application to provide an oxygen conserving device that can be connected with a conventional pressure/flow regulator with minor modification to the regulator.

It is a further object of the application to provide an oxygen conserving device that can be switched between a conserving mode and a continuous metering flow mode.

It also is an object of the invention to provide an oxygen conserving device that is responsive to a patient's inhalation to open a metering flow inlet to a delivery chamber from which oxygen is supplied to the patient.

It is an additional object of the invention to provide an oxygen conserving device that is reliable in operation, has good sensitivity, and is relatively easy to manufacture, assemble and repair.

BRIEF DESCRIPTION OF THE DRAWINGS

FIG. 2 is a partial cross-sectional elevational view showing the orientation of flow passages in the oxygen conserver;

FIG. 3 is a cross-sectional elevational view of the oxygen conserver in an oxygen conserving mode with two diaphragm valves open;

FIG. 6 is a partial cross-sectional elevational view of another embodiment and with passages diagrammatically shown for clarity of illustration;

FIG. 7 is a cross-sectional elevational view taken generally on line 7—7 of FIG. 6 showing a control valve in an oxygen conserving position;

DESCRIPTION OF REPRESENTATIVE EMBODIMENTS

Figure 1:
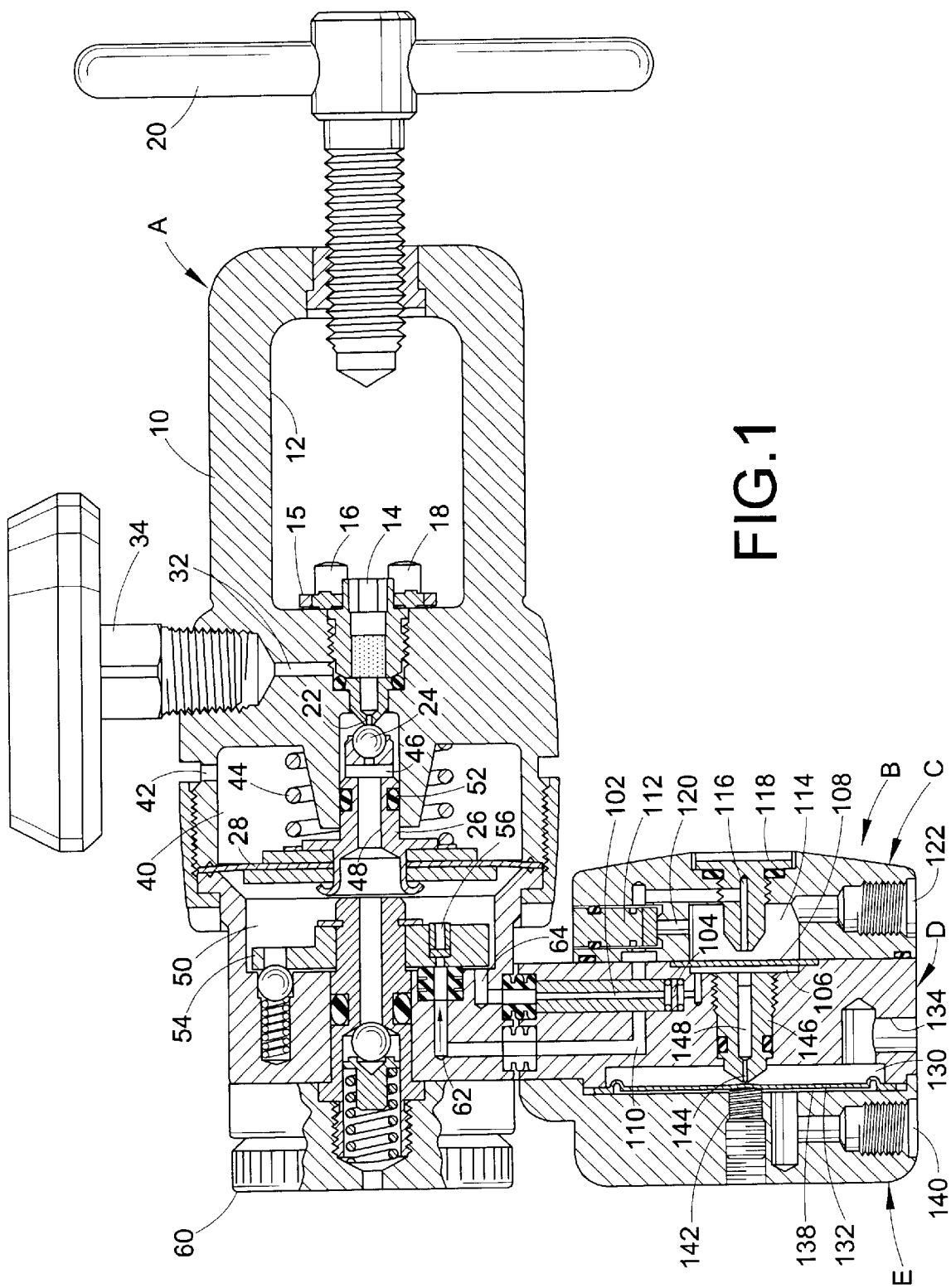
FIG. 1 is a cross-sectional elevational view of a pressure flow regulator having the oxygen conserver of the present application attached thereto, and with portions of flow passages in the oxygen conserver diagrammatically shown for clarity of understanding.

Referring now to the drawing, wherein the showings are for purposes of illustrating representative embodiments of the invention only and not for purposes of limiting same, FIG. 1 shows an oxygen pressure flow regulator A having an oxygen conserving device B in accordance with present application attached thereto. Oxygen pressure flow regulator A may be of any suitable type including that disclosed in U.S. Pat. No. 6,158,457 granted Dec. 12, 2000, the disclosure of which is hereby incorporated herein by reference.

The principal operating features of oxygen pressure flow regulator A will be described briefly to provide for a better understanding of the operation of oxygen conserving device B. Pressure flow regulator A includes a yoke 10 having an opening 12 for receiving a rectangular post valve on an oxygen cylinder. An inlet stub 14 on pressure flow regulator A is receivable in the outlet opening of the post valve on the oxygen cylinder. A pair of pins 16, 18 on pressure flow regulator A are receivable in bores on the post valve to facilitate alignment of inlet stub 14 with the post valve outlet. A T-handle 20 threadably attached to yoke 10 engages the post valve on an oxygen cylinder for drawing inlet stub 14 into the post valve outlet and ensuring a good seal for sealing washer 15.

Oxygen flows through the passage in inlet stub 14 to a control orifice 22 that is opened and closed by a ball 24 carried by a piston 26 attached to a diaphragm 28. A lateral passage 32 in communication with the passage in inlet stub 14 leads to a pressure gauge 34 that provides an indication of the amount of oxygen remaining in a cylinder to which the pressure flow regulator is attached.

An atmospheric chamber 40 on one side of diaphragm 28 is vented to atmosphere through a vent opening 42. A coil spring 44 in atmospheric chamber 40 normally biases diaphragm 28 and piston 26 to the left in FIG. 1 so that ball 24 moves to a position opening orifice 22. Oxygen then enters inlets 46 in piston 26 and flows through central piston passage 48 to a low pressure constant supply chamber 50 on the opposite side of diaphragm 28 from atmospheric chamber 40. When the pressure in chamber 50 exceeds the combined force of spring 44 and the gas pressure acting on piston seal 52, diaphragm 28 and piston 26 move to the right in FIG. 1 so that ball 24 closes orifice 22. Orifice 22 automatically is opened and closed in this manner to maintain a predetermined pressure range within low pressure constant supply chamber 50.

A rotatable orifice plate 54 within low pressure constant supply chamber 50 has a plurality of circumferentially-spaced orifices therein, only one of which is shown at 56. A rotatable flow rate selector knob 60 is manually operable to rotate orifice plate 54 for selectively aligning different orifices with metered flow outlet passage 62. Orifice plate 54 also is rotatable to an off position in which no orifice is aligned with passage 62 which is then closed. A ball detent mechanism 63 releasably retains orifice plate 54 in a selected position. A low pressure outlet passage 64 communicates with low pressure constant supply chamber 50.

By way of example, an oxygen cylinder to which pressure flow regulator A is attached may have an internal pressure of around 2,200 psi. The pressure within low pressure constant supply chamber 50 may be around 20–50 psi. Each of the plurality of orifices in orifice plate 54 has a different size for selectively providing metered flow of oxygen at different flow rates as set by operator adjustment of knob 60.

Oxygen conserving device B is assembled from three sections including a delivery section C, a central supply section D and a sensing section E. The three sections are bolted or otherwise suitably secured together. Conserver B is attached to regulator A with suitable compression sleeves therebetween in the flowpath of the connected passages.

Conserver first supply pressure passage 102 supplies oxygen from low pressure constant supply chamber 50 through outlet passage 64 and past a flow reducer 104 to a supply pressure chamber 106 in supply section D on the left side of a delivery diaphragm 108 that has its periphery sealingly secured between delivery section C and supply section D.

A conserver second supply passage 110 is an oxygen metering flow passage and is connected with regulator metered flow outlet passage 62 for supplying metered flow past a control valve 112 to a delivery chamber 114 through a conserving metering flow passage 116 in insert 118. Delivery chamber 114 is in delivery section C on the opposite side of delivery diaphragm 108 from supply pressure chamber 106.

Control valve 112 is movable from the oxygen conserving position shown to an alternate continuous metering flow position for providing continuous flow from conserver metering flow passage 110 directly to delivery chamber 114 through a continuous metering flow passage 120. An outlet port 122 communicates with delivery chamber 114 for supplying oxygen to a patient.

An atmospheric chamber 130 is provided in supply section D on the right side of sensing diaphragm 132 in FIG. 1, and the diaphragm periphery is sealingly secured between supply section D and sensing section E. An atmospheric vent port 134 connects atmospheric chamber 130 to atmosphere. A sensing chamber 138 in sensing section E on the left side of diaphragm 132 communicates with a sensing port 140 for sensing inhalation by a patient. Sensing chamber 138 accumulates a partial vacuum during inhalation by a patient and accumulates positive pressure during exhalation by a patient. Sensing diaphragm 132 is biased to the right in FIG. 1 by a coil spring 142 so that the diaphragm normally closes an orifice 144 in an insert 146 having a vent passage 148 communicating with supply pressure chamber 106.

One hose of a dual cannula is connected with each of outlet port 122 and sensing port 140 so that both ports simultaneously are in communication with the patient at all times.

Prior to pressurization of pressure flow regulator A, delivery diaphragm 108 is in the open position shown in FIG. 1 while sensing diaphragm 132 is in a closed position against insert 146 by the force of coil spring 142 for closing orifice 144 and vent passage 148.

When flow regulator A is pressurized by opening the post valve on an oxygen cylinder, oxygen flows through conserver first low pressure constant supply passage 102 to supply pressure chamber 106 and provides a closing force on delivery diaphragm 108 for moving same to a closed position against insert 118 for closing oxygen metering flow passage 116.

At this point, a user will select the flow rate by operating selector knob 60 on pressure flow regulator A. Oxygen then will flow through the selected orifice 56 in the pressure regulator to conserver metering flow passage 110 and toward delivery chamber 114 through passage 116 in insert 118. Flow will stop when the pressure within oxygen metering flow passage 116 equalizes with the regulator delivery pressure in low pressure constant supply chamber 50 which also is the pressure in supply pressure chamber 106 on the opposite side of delivery diaphragm 108 from delivery chamber 114.

Upon inhalation by a patient who is connected by a dual cannula with both sensing port 140 and delivery port 122, a partial vacuum accumulates in sensing chamber 138 on the left side of sensing diaphragm 132. This causes sensing diaphragm 132 to move to the left in FIG. 1 against the biasing force of spring 142 and opens orifice 144 in insert 146 so that the pressure accumulated within supply pressure chamber 106 on the left of delivery diaphragm 108 is vented to atmosphere through atmospheric chamber 130 and atmospheric vent port 134.

As the pressure in supply pressure chamber 106 decreases, the closing force on delivery diaphragm 108 decreases and allows same to open oxygen metering flow inlet passage 116 by moving away from engagement with insert 118. Oxygen then flows into delivery chamber 114 through oxygen metering flow inlet passage 116 in insert 118 and to the patient through the cannula connected with outlet port 122.

Conserver flow reducer 104 in conserver first supply passage 102 controls the flow rate to supply pressure chamber 106 for minimizing the amount of oxygen lost to atmosphere during inhalation when supply pressure chamber 106 is purged to atmosphere through passage 148 and orifice 144 in insert 146, and then through atmospheric chamber 130 and vent port 134. The flow reducer orifice also provides an adequate pressure drop in supply pressure chamber 106 upon inhalation to allow delivery diaphragm 108 to remain open for a sufficient time to provide delivery of oxygen through oxygen metering flow passage 116 to delivery chamber 114 and to the patient through outlet port 122.

When inhalation stops, the partial vacuum in sensing chamber 138 decreases until it reaches atmospheric pressure and thereby allows sensing diaphragm 130 to return to its closed position in engagement with insert 146 by virtue of the biasing force of spring 142. Pressure again will accumulate in supply pressure chamber 106 to move delivery diaphragm 108 to the right and close oxygen metering flow inlet passage 116 in insert 118. Flow to metering flow inlet passage 116 also continues until its pressure equalizes with the delivery pressure of the regulator in regulator chamber 50 and in supply pressure chamber 106. This cycle is repeated with each breath of the patient.

Figure 4:
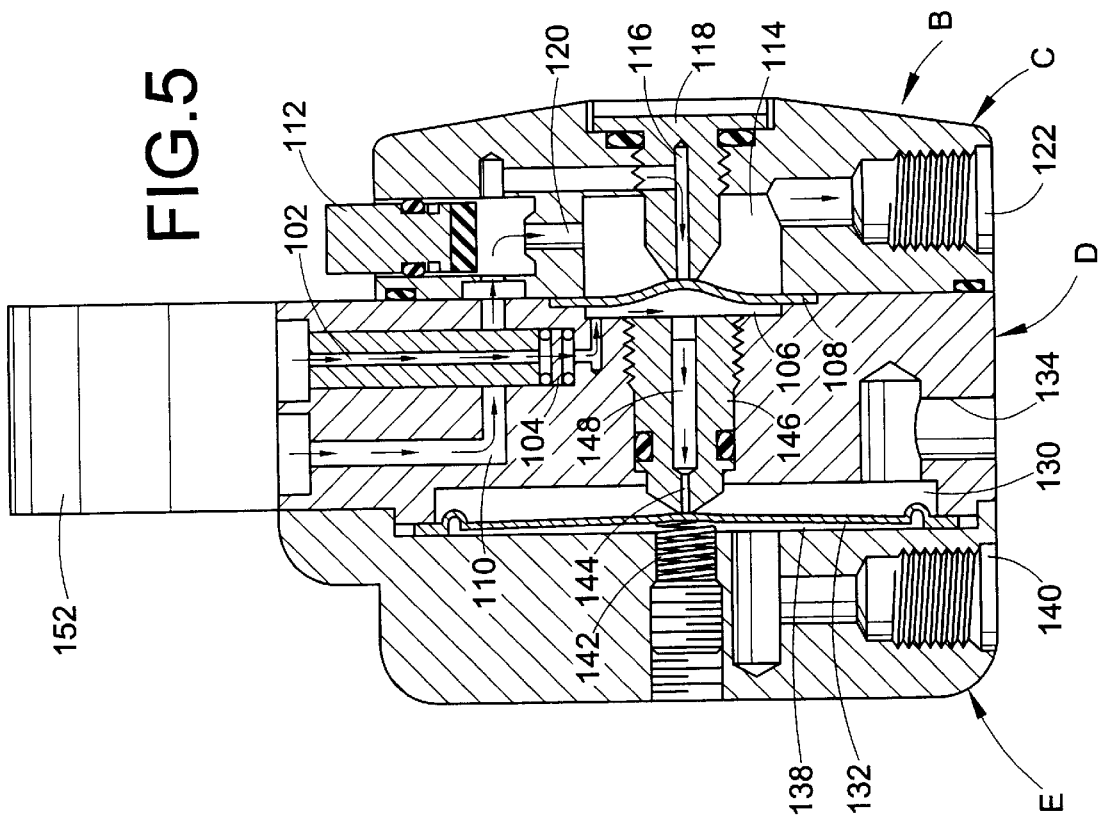
FIG. 4 is a cross-sectional elevational view similar to FIG. 3 with both diaphragm valves closed.
Figure 5:
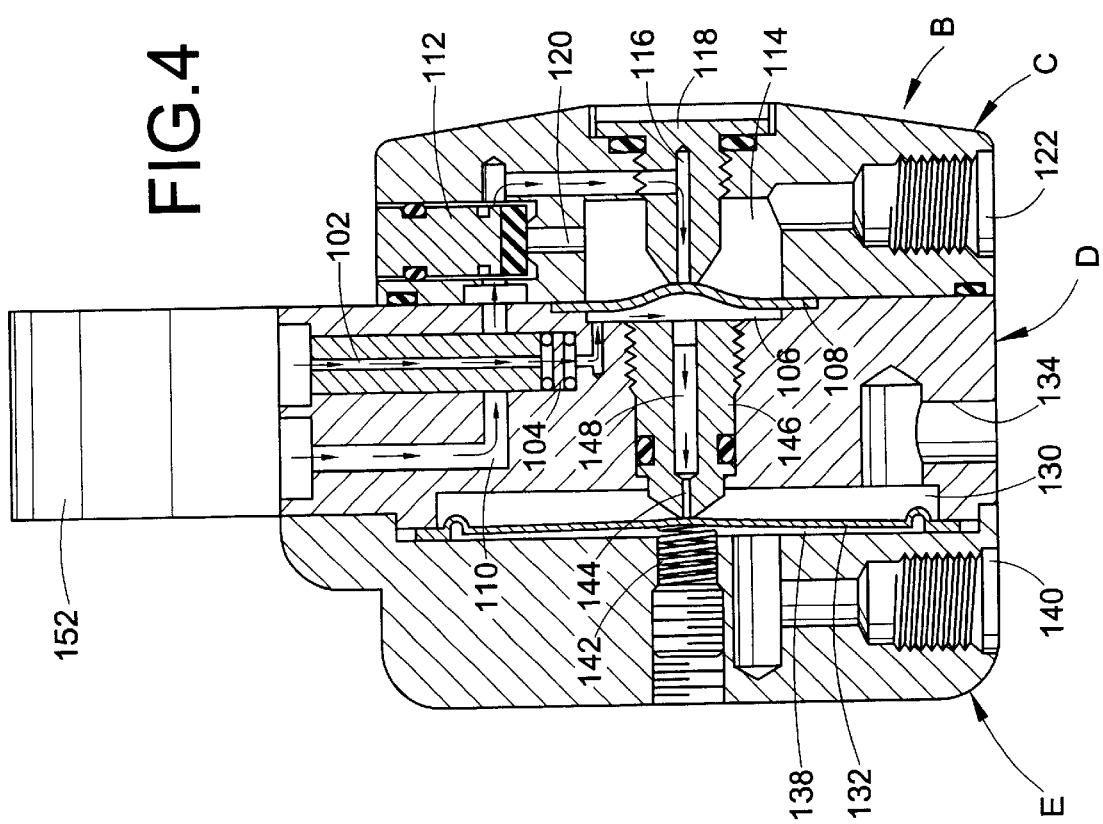
FIG. 5 is a cross-sectional elevational view similar to FIG. 3 and showing the oxygen conserver in a continuous flow mode.

FIG. 3 shows the oxygen conserving device with control valve 112 in a conserving position. The arrows show the direction of flow of oxygen through the various passages and ports. FIG. 4 shows the conserver with control valve 112 in the conserving position and with both diaphragms in closed positions. FIG. 5 shows control valve 112 in its alternative position for opening bypass passage 120 for supplying continuous metering flow of oxygen to the patient.

FIG. 2 shows oxygen conserver device B as having a generally U-shaped yoke portion 152 with countersunk holes 154, 156 therein for receiving bolts to attach the conserver to the bonnet of the pressure flow regulator A. FIG. 2 is a more accurate depiction of the path of metering flow passage 110 which is diagrammatically shown in FIG. 1 for clarity of illustration.

FIGS. 6–9 show another embodiment in which the principal difference from the embodiment of FIGS. 1–5 concerns the control valve. Therefore, common numerals are used to identify common parts in both embodiments. In the embodiment of FIGS. 6–9, control valve 112a reciprocates longitudinally between the oxygen conserving position of FIG. 7 and the constant flow position of FIG. 8. In FIG. 7, conserver metering flow passage 110 intersects with control valve 112a between seals 160, 162 to communicate past the peripheral clearance around the control valve with delivery chamber 114 through passages 110a, 110b, 110c and oxygen metering flow passage 116 in insert 118.

Figure 9:
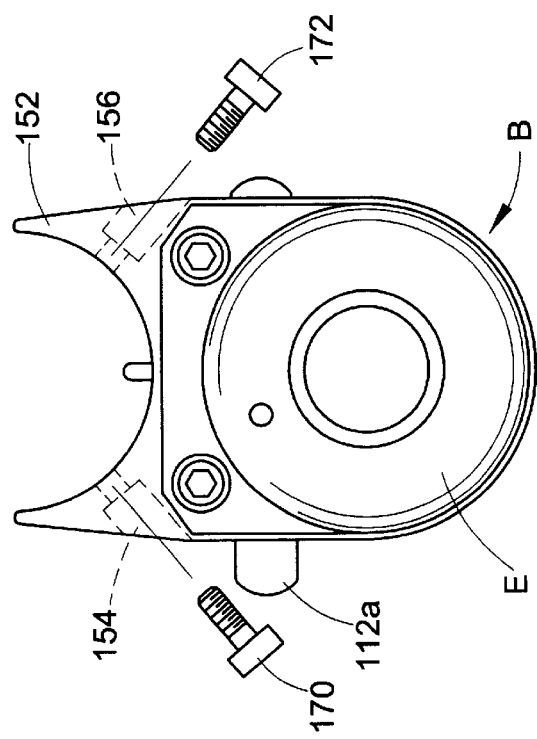
FIG. 9 is an end elevational view taken generally on line 9—9 of FIG. 6.
Figure 8:
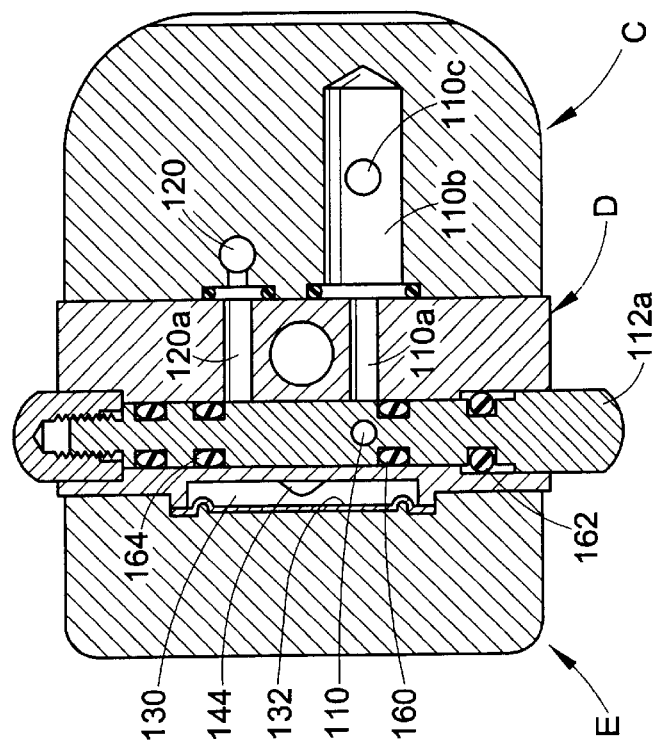
FIG. 8 is a view similar to FIG. 7 showing the control valve in a continuous flow mode.

In the continuous metering flow position of FIG. 8, conserver metering flow passage 110 is located between seals 160, 164 so that oxygen is supplied directly to delivery chamber 114 through bypass passage 120, 120a. In the embodiment of FIG. 6, hose barbs 122a, 140a respectively are attached to outlet port 122 and sensing port 140 for receiving hoses on the dual cannula. FIG. 9 shows the bolts 170, 172 that are receivable in the countersunk holes 154, 156 for attaching the oxygen conserver device to the bonnet of the pressure flow regulator.

Delivery diaphragm 108 functions as a main control valve while cycling between open and closed positions to deliver oxygen in step with a patient's inhalation cycle. Sensing diaphragm 132 also functions as a valve by cycling between open and closed positions, and opens in step with a patient's inhalation cycle. Exhalation by the patient pressurizes sensing chamber 138 to assist spring 142 in returning the diaphragm to a closed position for closing outlet 144 of vent passage 148.

When the control valve 112, 112a is moved to a continuous metering flow position, sensing diaphragm 132 and delivery diaphragm 108 continue to cycle with the patient's inhalation/exhalation but this has no effect on the continuous delivery of oxygen to the patient.

A number of advantageous features of the oxygen flow control device of the present application will be mentioned simply by way of example and not by way of limitation. It will be recognized that the invention may be practiced within the scope of the claims without necessarily using these features. The oxygen conserver of the present application uses a dual tube cannula. The two tubes may be side-by-side or coaxial and both are simultaneously connected with the patient. For some purposes, sensing port 140 and delivery port 122 may be connected by a T-fitting with a single cannula so that the patient is connected with both ports by the single cannula.

The conserver has two ports, one for delivering oxygen to a patient and the other for sensing inhalation and exhalation by the patient. The sensing port is not connected with the oxygen outlet port.

The control valve, which switches the oxygen conserver between a continuous mode and a conserving mode, does not pressurize the sensing chamber. The control valve is independent of the pressure inlet to the sensing chamber, and the control valve bypasses the main delivery diaphragm in the delivery chamber to provide a direct path to the oxygen outlet port.

The oxygen conserving unit is independent of the pressure flow regulator, and is attached to the regulator which is upstream of the conserving unit.

The oxygen conserver does not use a spring in the oxygen delivery chamber. The oxygen inlet passages for metering flow and constant supply pressure are independent of one another and do not connect within the conserver body. The oxygen delivery chamber is continuously vented to the patient through the outlet port.

The delivery diaphragm does not require balanced input pressure on both sides of the diaphragm. The oxygen conserver/pressure flow regulator is not combined and enclosed within a common housing, and is designed so that a conserving unit can be added onto a slightly modified production pressure/flow regulator.

The conserving unit does not have an oxygen delivery chamber that stores oxygen.

The conserver provides a flow path between a pressure source or inlet and an oxygen outlet port with a delivery diaphragm control valve between the pressure source and oxygen outlet.

The conserver does not require spring compensation for biasing the oxygen delivery diaphragm. The conserver does not have a bypass passageway communicating pressurized oxygen from the supply pressure passage to the delivery chamber and has an independent metering flow pressure input to the oxygen delivery chamber.

Within the conserving device, the oxygen delivered to the supply pressure chamber does not communicate with the oxygen that flows to the patient. The delivery diaphragm within the conserving device separates the source oxygen that flows to the patient from the supply pressure oxygen. The oxygen conserving unit is designed for integration with a pressure/flow regulator.

Although the invention has been shown and described with reference to representative embodiments, it is obvious that alterations and modifications will occur to others skilled in the art upon the reading and understanding of this application. Therefore, it is to be understood that the invention may be practiced otherwise than as specifically described herein while remaining within the scope of the claims.

I claim:

1. Apparatus comprising:
   an oxygen delivery device having a delivery chamber on one side of a delivery diaphragm;
   an oxygen metering flow inlet to said delivery chamber;
   said delivery diaphragm being movable between positions opening and closing said oxygen metering flow inlet;
   a continuous metering flow inlet to said delivery chamber in addition to said oxygen metering flow inlet that is opened and closed by said delivery diaphragm; and
   a manually operable control valve that selectively opens or closes said continuous metering flow inlet.

2. The apparatus of claim 1 wherein said oxygen delivery device has a generally U-shaped yoke for attaching the oxygen delivery device to a pressure regulator, said oxygen metering flow inlet being at one end of an oxygen metering flow passage that has an opposite open end within said yoke for communication with a low pressure constant supply chamber on a pressure regulator when the yoke is attached to the pressure regulator.

3. Apparatus comprising:
   an oxygen delivery device having an oxygen delivery port and a sensing part that senses inhalation by a patient;
   both of said ports being simultaneously connectable with a patient;
   an oxygen delivery chamber communicating with said oxygen delivery port;
   an oxygen metering flow inlet to said oxygen delivery chamber;
   a delivery diaphragm that opens and closes said oxygen metering flow inlet;
   an oxygen supply pressure chamber on the opposite side of said delivery diaphragm from said oxygen delivery chamber;
   both said oxygen delivery chamber and said oxygen supply pressure chamber being connected in fluid communication with a common low pressure constant supply chamber on a pressure regulator;
   a continuous metering flow inlet to said delivery chamber in addition to said oxygen metering flow inlet that is opened and closed by said delivery diaphragm; and
   a manually operable control valve within said oxygen delivery device for opening and closing said continuous metering flow inlet.

4. Apparatus comprising:
   an oxygen delivery device having an oxygen delivery port and a sensing port that senses inhalation by a patient;
   both of said ports being simultaneously connectable with a patient;
   an oxygen delivery chamber communicating with said oxygen delivery port;
   an oxygen metering flow inlet to said oxygen delivery chamber;
   a delivery diaphragm that opens and closes said oxygen metering flow inlet;
   an oxygen supply pressure chamber on the opposite side of said delivery diaphragm from said oxygen delivery chamber;
   an oxygen metering flow passage communicating with said delivery chamber through said oxygen metering flow inlet;
   a supply pressure passage communicating with said supply pressure chamber;
   both said oxygen delivery chamber and said oxygen supply pressure chamber being connected in fluid communication with a common low pressure constant supply chamber on a pressure regulator through said oxygen metering flow passage and said supply pressure passage;
   an attachment device on said oxygen delivery device for attaching the oxygen delivery device to a pressure regulator; and
   said oxygen metering flow passage and said supply pressure passage opening outwardly at said attachment device for communication with a low pressure constant supply chamber on the pressure regulator when the attachment device is secured to the pressure regulator.

5. The apparatus of claim 4 wherein said attachment device is a generally U-shaped yoke and said oxygen metering flow passage and said supply pressure passage open outwardly within said yoke for connection with the low pressure constant supply chamber on the pressure regulator when the yoke is attached to the pressure regulator.

6. Apparatus comprising:
   an oxygen delivery device having an oxygen delivery port and a sensing port that senses inhalation by a patient;
   both of said ports being simultaneously connectable with a patient;
   an oxygen delivery chamber communicating with said oxygen delivery port;
   an oxygen metering flow inlet to said oxygen delivery chamber;
   a delivery diaphragm that opens and closes said oxygen metering flow inlet;

an oxygen supply pressure chamber on the opposite side of said delivery diaphragm from said oxygen delivery chamber;

both said oxygen delivery chamber and said oxygen supply pressure chamber being connected in fluid communication with a common low pressure constant supply chamber on a pressure regulator;

said oxygen conserving device being assembled into a unitary assembly from three individual cooperating sections that are secured together and include an end delivery section, a central supply section and an end sensing section;

a delivery diaphragm between said delivery and supply sections;

a delivery chamber in said delivery section on one side of said delivery diaphragm;

a supply pressure chamber in said supply section on the opposite side of said delivery diaphragm;

a supply pressure passage in said supply section communicating with said supply pressure chamber;

a metering flow passage in said supply section communicating with said delivery chamber through said oxygen metering flow inlet;

said oxygen delivery port being in said delivery section in communication with said delivery chamber;

a sensing diaphragm between said central supply and end sensing sections;

an atmospheric chamber in said supply section on one side of said sensing diaphragm;

an atmospheric port in said supply section communicating with said atmospheric chamber;

a sensing chamber in said sensing section on the opposite side of said sensing diaphragm from said atmospheric chamber;

said sensing port being in said sensing section in communication with said sensing chamber;

a vent passage in said central supply section communicating between said supply pressure chamber and said atmospheric chamber;

said sensing diaphragm being biased to a position closing said vent passage;

wherein pressure in said supply pressure chamber causes said delivery diaphragm to close said oxygen metering flow inlet passage;

wherein inhalation by a patient draws a partial vacuum in said sensing chamber through said sensing port to move said sensing diaphragm to a position opening said vent passage;

wherein opening of said vent passage depressurizes said supply pressure chamber by venting same to atmosphere through said vent passage, said atmospheric chamber and said atmospheric port;

wherein venting of said supply pressure port causes said delivery diaphragm to move to a position opening said oxygen metering flow inlet passage; and wherein opening of said oxygen metering flow inlet supplies oxygen to said oxygen delivery chamber for delivery to a patient through said oxygen delivery port;

a continuous metering flow inlet to said delivery chamber in addition to said oxygen metering flow inlet that is opened and closed by said delivery diaphragm;

a continuous metering flow passage communicating with said continuous metering flow inlet;

a manually operable control valve in said continuous metering flow passage; and said control valve being movable to a continuous metering flow position for supplying a continuous metering flow of oxygen to said delivery chamber through said continuous metering flow inlet independently of oxygen flowing through said oxygen metering flow inlet by operation of said delivery and sensing diaphragms.

7. The apparatus of claim 6 wherein said manually operable control valve is within said end delivery section.

8. The apparatus of claim 6 wherein said manually operable control valve is within said central supply section.

9. Apparatus comprising:

an oxygen conserving device assembled into a unitary assembly from three individual sections that are secured together and include an end delivery section, a central supply section and an end sensing section;

a delivery diaphragm between said delivery and supply sections;

a delivery chamber in said end delivery section on one side of said delivery diaphragm;

a supply pressure chamber in said central supply section on the opposite side of said delivery diaphragm from said delivery chamber;

a supply pressure passage in said supply section communicating with said supply pressure chamber;

an oxygen metering flow passage communicating with said delivery chamber through an oxygen metering flow inlet and through a continuous metering flow inlet;

an oxygen outlet port in said delivery section communicating with said delivery chamber;

a sensing diaphragm between said supply and sensing sections;

an atmospheric chamber in said supply section on one side of said sensing diaphragm;

an atmospheric vent port in said supply section communicating with said atmospheric chamber;

a sensing chamber in said end sensing section on the opposite side of said sensing diaphragm from said atmospheric chamber;

a sensing port in said sensing section communicating with said sensing chamber;

a vent passage in said supply section communicating between said supply pressure chamber and said atmospheric chamber;

said sensing diaphragm being biased to a position closing said vent passage;

wherein pressure in said supply pressure chamber causes said delivery diaphragm to close said oxygen metering flow inlet;

wherein inhalation by a patient draws a partial vacuum in said sensing chamber through said sensing port to move said sensing diaphragm to a position opening said vent passage;

wherein opening of said vent passage depressurizes said supply pressure chamber by venting same to atmosphere through said vent passage, said atmospheric chamber and said atmospheric vent port;

wherein venting of said supply pressure port causes said delivery diaphragm to move to a position opening said oxygen metering flow inlet; arid wherein opening of said oxygen metering flow inlet supplies oxygen to said oxygen delivery chamber for delivery to a patient through said oxygen delivery port;

a manually operable control valve in said oxygen metering flow passage;

said control valve having a closed position blocking flow through said continuous metering flow inlet while allowing flow through said oxygen metering flow inlet and being movable to an open continuous metering flow position for supplying a continuous metering flow of oxygen to said delivery chamber through said continuous metering flow inlet independently of operation of said delivery and sensing diaphragms to supply oxygen to said delivery chamber through said oxygen metering flow inlet which is independent from said continuous metering flow inlet; and said oxygen metering flaw passage and said supply pressure passage opening directly outwardly from said central supply section for communication with a low pressure constant supply chamber on a pressure regulator when the central supply section is attached to the pressure regulator.

10. The apparatus of claim 9 wherein said manually operable control valve is within said end delivery section.

11. The apparatus of claim 9 wherein said manually operable control valve is within said central supply section.

12. The apparatus of claim 9 including an attachment device on said central supply section for attaching the central supply section to a pressure regulator, the oxygen metering flow passage and the supply pressure passage opening outwardly through the attachment device.

13. The apparatus of claim 9 wherein said attachment device is a generally U-shaped yoke and said oxygen metering flow passage and said supply pressure passage open outwardly within said yoke for connection with the low pressure constant supply chamber on the pressure regulator when the yoke is attached thereto.

14. The apparatus of claim 13 wherein said yoke is a part of said central supply section of said unitary assembly.

* * * * *

UNITED STATES PATENT AND TRADEMARK OFFICE
CERTIFICATE OF CORRECTION

PATENT NO.   : 6,612,307 B2
DATED        : September 2, 2003
INVENTOR(S)  : Douglas R. Byrd It is certified that error appears in the above-identified patent and that said Letters Patent is hereby corrected as shown below:

Column 7,
Line 60, change "part" to -- port --

Column 10,
Line 64, change "arid" to -- and --

Signed and Sealed this

Twenty-first Day of October, 2003

JAMES E. ROGAN
*Director of the United States Patent and Trademark Office*